United States Patent [19]

Shah

[11] 4,366,581
[45] Jan. 4, 1983

[54] ELLIPTICAL SUTURING CUFF

[75] Inventor: Suresh T. Shah, Eagan, Minn.

[73] Assignee: Medical Incorporated, Iver Grove, Minn.

[21] Appl. No.: 298,656

[22] Filed: Sep. 2, 1981

[51] Int. Cl.³ .............................................. A61F 1/22
[52] U.S. Cl. ......................................................... 3/1.5
[58] Field of Search ..................... 3/1.5, 1; 128/334 R

[56] References Cited

U.S. PATENT DOCUMENTS

| | | | |
|---|---|---|---|
| 3,739,402 | 6/1973 | Cooley et al. | 3/1.5 |
| 3,859,668 | 1/1975 | Anderson | 3/1.5 |
| 4,197,593 | 4/1980 | Kaster et al. | 3/1.5 |
| 4,240,161 | 12/1980 | Huffstutler et al. | 3/1.5 |
| 4,306,319 | 12/1981 | Kaster | 3/1.5 |

Primary Examiner—Ronald L. Frinks
Attorney, Agent, or Firm—Bruce A. Jagger

[57] ABSTRACT

An elliptical suturing cuff for a mitral prosthetic heart valve with a round planform. The suturing cuff is constructed from a single piece of seamless knit tubing. The radially enlarged portions of the cuff are positioned generally adjacent to the pivot and retaining structure on the valve base.

5 Claims, 6 Drawing Figures

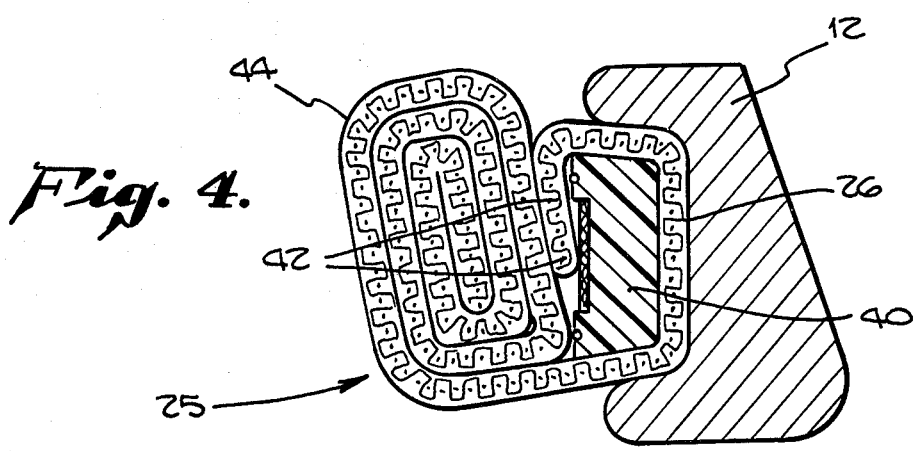
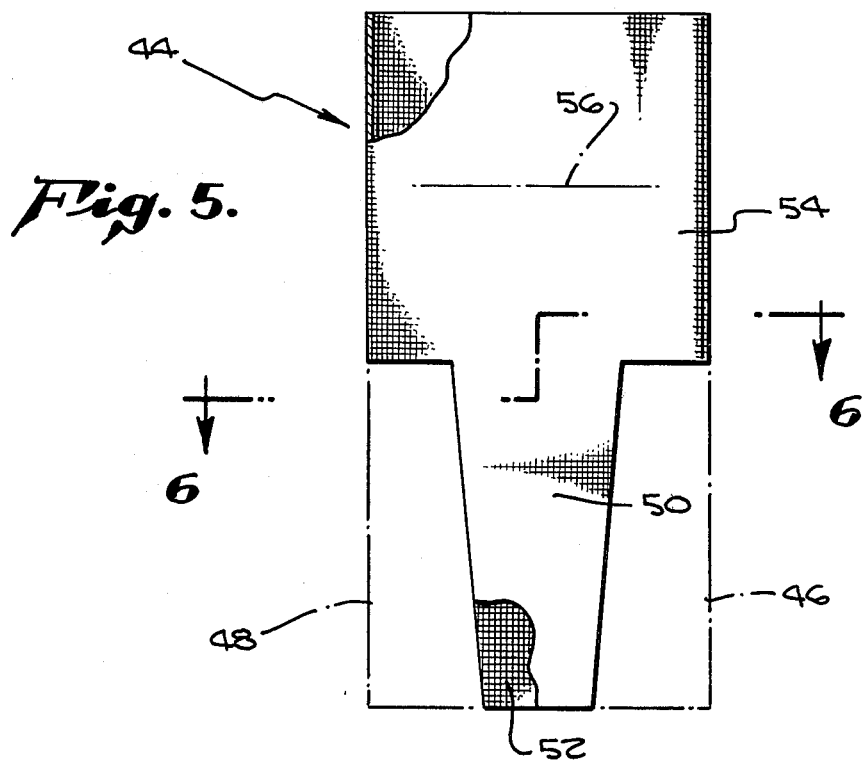
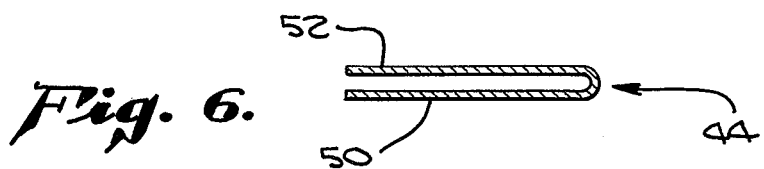

ELLIPTICAL SUTURING CUFF

The present invention relates to suturing cuffs for heart valves and in particular relates to elliptical suturing cuffs for mitral heart valves.

Previously, considerable difficulty had been encountered in the implantation of prosthetic mitral heart valves. The accurate placement of mitral heart valve cuffs and good seating of these cuffs to the annulus are necessary so as to avoid creating conditions which adversely influence the functioning of the valve. Such adverse conditions include paravalvular leakage which may seriously impair the performance of the valve and may even lead to thrombus formation and other problems. Distorting the annulus shelf of tissue during suturing to conform to the shape of a round suturing cuff may cause difficulties. Tissue may in time grow over the cuff so as to interfere with the operation of the valve. This is particularly serious where a mechanical valve is implanted. These and other disadvantages of the prior art have been overcome according to the present invention wherein a knit tubing structure is formed into a suturing cuff. The tubing contains additional material located in such locations that when the cuff is formed it will have an elliptical planform. The elliptical cuff provides several advantages during its implantation by a surgeon and its subsequent usage.

Mechanical heart valves are preferably round in planform. This is desirable for reasons of ease and reliability in manufacturing and safety and longevity in use. Round planform valves are easier to mass produce to tightly controlled specifications than are other planforms. Round planform valves permit their valving elements to rotate, thus reducing the chance of thrombus formation and causing the wear to be distributed over the valving member.

There is a problem with the use of round planform heart valves in the mitral position. The mitral shelf of tissue to which the heart valve must be sutured is approximately elliptical. Suturing a round planform heart valve onto an elliptical shelf of tissue creates a potential for the distortion of the shelf of tissue. This may result in paravalvular leaks, thrombus formation and impaired functioning of the heart.

A problem which is occasionally encountered with mechanical heart valves is that tissue grows over the base of the valve into a location where it impairs the functioning of the valving element. This is particularly dangerous when the ingrowth encroaches in the area where the valving element contacts the base or retaining structure during opening or closing movement. This may cause the valving element to stick in one position. The use of an elliptical cuff which is radially enlarged in certain areas provides a solution to the problem of tissue encroachment by orienting the valve with respect to the major axis of the elliptical cuff so that the crucial areas of the valve are substantially aligned with that major axis. The tissue thus has farther to grow before encountering vital areas of the valve. Some ingrowth of tissue is very desirable. It is only excessive ingrowth which presents a problem when it hinders the valve's moving parts.

In general, heart valve cuffs preferably are constructed from a single piece of fabric. This fabric may conveniently be in the form of a seamless tube. In general, the seamless tubing is formed from multifilament twisted or braided yarn utilizing from about 40 to 60 needles per inch. In general, staple yarns are less desirable because of the possibility of shedding short lengths of fiber into the blood stream.

The knit structure has a predetermined porosity which it tends to hold in use. This is significant in promoting the uniform in-growth of tissue into the suturing cuff. Variations in the porosity or distortions introduced during manufacturing or implantation result in nonuniform tissue growth and may even result in perivalvular leaks through the cuff where the pores have been altered so that they are either too large or too small.

The suturing procedures are also facilitated where a uniform texture is exhibited by the cuff. Variations in texture and in the response of the cuff to suturing may result in non-uniform spacing of the sutures which may also give rise to perivalvular leaks. The use of seamless knit tubing for incorporation into a suturing cuff is advantageous, as contrasted with the use of flat knit stock, because there are no irregularities in the seamless tubing caused by the joining together of the edges of flat stock. The construction of the cuff from a single piece of material is advantageous in reducing the number of possible errors in production and in reducing the potential for a piece being dislodged from the cuff.

In the manufacturing of suturing cuffs from seamless tubing a predetermined length of seamless tubing is placed over the valve, secured there in place, and is then folded up according to predetermined folding procedures so as to produce a cuff having the desired characteristics and configurations. In the folding of the sleeve so as to form the cuff, it is preferred to maintain the various wales of the knit structure in vertical alignment from one fold to another. Shifting of the wales out of alignment tends to distort the cuff material so that its porosity is changed in unpredictable ways, and the feel of the cuff is also changed so as to make suturing difficult. The tubing from which the cuff is formed is preferably cut so that excess integral material is present along the major axis of the elliptical cuff. This excess material is integral with and of the same characteristics as the balance of the cuff. When this excess material is folded into the cuff, the cuff's characteristics are maintained substantially uniform throughout and significant distortions are avoided. The integral nature of the excess material contributes significantly to maintaining the uniformity, safety and ease of construction of the cuff.

The cuff is generally proportioned so that the ratio of the length of the minor axis of the elliptical cuff to the length of the major axis is from about 0.80 to 0.93 and preferably from about 0.85 to 0.91. Thus, for a typical 25 millimeter pivoting disc mechanical mitral valve, the minor diameter is 29.8 millimeters and the major diameter is 33.5 millimeters; for a typical 27 millimeter valve, the minor and major diameters are 31.6 and 36.4, respectively; for a typical 29 millimeter valve, the diameters are 35.8 and 39.1, respectively; and for a typical 31 millimeter valve, the diameters are 37.6 and 41.5, respectively.

Previous expedients included the use of an approximately elliptical planform mechanical valve where the valving member did not rotate in the base and the cuff was of approximately the same radial thickness throughout. This is to be contrasted with the present invention where the advantages of a round planform valve and an elliptical cuff of varying radial thickness are enjoyed.

During implantation, the elliptical planform of the cuff permits the surgeon to accurately and rapidly position and suture the cuff to the elliptical mitral shelf of tissue. Speed and accuracy are both very important in heart valve implantation procedures.

The materials utilized in the manufacture of the cuff are well known biocompatible materials such as polyester and Teflon materials.

Referring particularly to the drawings which are submitted for purposes of illustration and not limitation, there is illustrated:

FIG. 4 is an enlarged cross-sectional view of a portion of the base and suturing cuff of the heart valve of FIG. 1, taken along the major diameter of the cuff;

FIG. 5 is a plan view of a flattened seamless knit tube with certain panels of material cut away in preparation for the formation of an elliptical suturing cuff; and FIG. 6 is a cross-sectional view taken along line 6—6 in FIG. 5.

Figure 1:
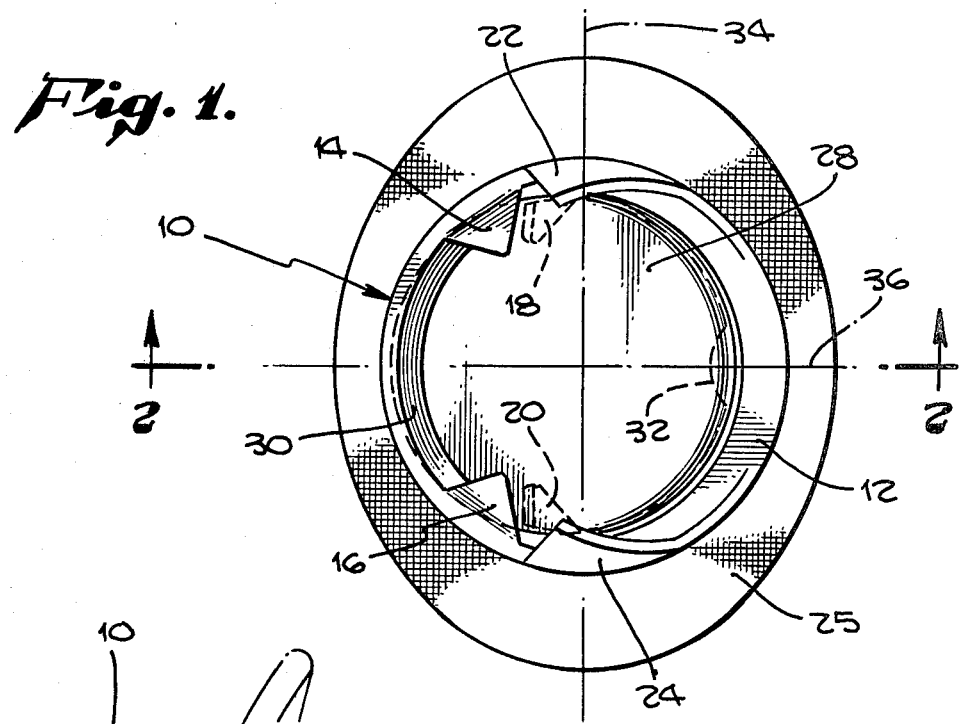
FIG. 1 is a plan view of a free floating pivotal disc heart valve which incorporates an elliptical suturing cuff of the present invention with a round planform valve.

Referring particularly to the drawings, there is illustrated a pivoting disc free floating heart valve in which the disc pivots within the flow passage of the valve indicated generally at 10. The valve includes an annular base 12. Integral with the base 12 are opening pivots 14 and 16, closing pivots 18 and 20, and disc retainers 22 and 24. A suture cuff retainer groove 26 is provided on the exterior of the valve base so as to permit attachment of an elliptical suturing cuff 25. A round disc 28 is retained in operative relationship with base 12 so that it opens and closes responsive to the flow of fluid through the valve 10. The blood flows through generally annular passage 30 in one direction. Disc 28 pivots freely under the force of forward flowing blood to open the valve so as to permit blood to flow therethrough. As soon as blood begins to flow in the reverse direction through the valve, it carries disc 28 with it so as to close the valve and prevent the flow of blood therethrough. A disc stop 32 is provided to insure that the disc rests in the desired location in the closed configuration and does not pivot too far in the closing phase. The valve is constructed of rigid antithrombic materials, such as titanium and carbon. The nature of the materials and the design and configuration of the device are such that a perfect seal is not generally achieved, and there is some weeping around the edges of the disc in the closed position. The volume of regurgitation through the valve in the closed configuration is carefully controlled so that it does not significantly increase the amount of work required by the heart. Any uncontrolled paravalvular leakage places an excess and often dangerous burden on the heart.

Figure 2:
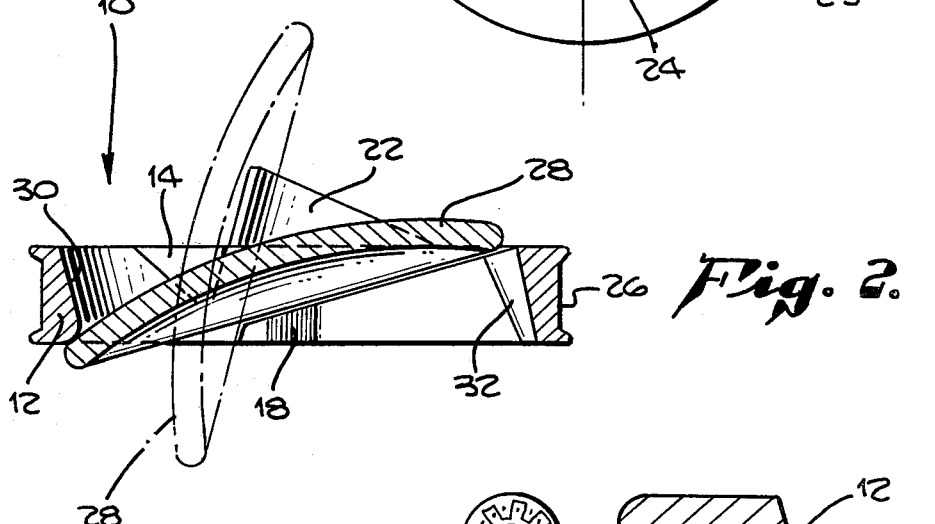
FIG. 2 is a cross-sectional view taken along line 2—2 in FIG. 1 with the suturing cuff removed.

The size of the opening and closing pivots and the disc retainers has been shown enlarged in proportion to the base for the purposes of simplifying illustration of the device. During the opening phase of the valve's action, the disc pivots generally chordally within passage 30 around opening pivots 14 and 16 between the closed and opened positions, as illustrated particularly in FIG. 2. During the closing phase the disc 28 pivots generally chordally within passage 30 about the closing pivots 18 and 20. The disc is retained in an operative position during the opening phase and while in the open configuration by disc retainers 22 and 24. The disc is retained in operative position during the closing phase by contact between the periphery of the disc 28 and the wall between the opening and closing pivots. The edge of the disc contacts the wall between pivots 14 and 18 on one side and 16 and 20 on the other side of base 12 and remains in contact with this area as it pivots through the closing phase. Slight lateral movement of the disc is permitted during the opening and closing phases so as to permit the disc to move freely. The disc rotates about its own axis of rotation during operation so as to distribute wear and avoid the formation of thrombi. The disc must have a round planform in order to accomplish this important wear distribution function.

The round valve is oriented so that the radially enlarged portions of the elliptical cuff are adjacent to the areas where the disc retainers and pivots are located. The major diameter 34 of cuff 25 is preferably generally parallel to the instantaneous chords about which disc 28 pivots. Minor diameter 36 of cuff 25 generally extends perpendicular to the instantaneous pivotal chords of disc 28. Any tissue which grows over base 12 into passage 30 along minor diameter 36 may cause problems, but is not generally catastrophic. Ingrown tissue that reaches the area of the disc retainers or pivots may block the movement of the disc with fatal consequences. The added measure of protection which is provided by the radial enlargement of the cuff along the major diameter 34 increases the reliability of the valve.

Figure 3:
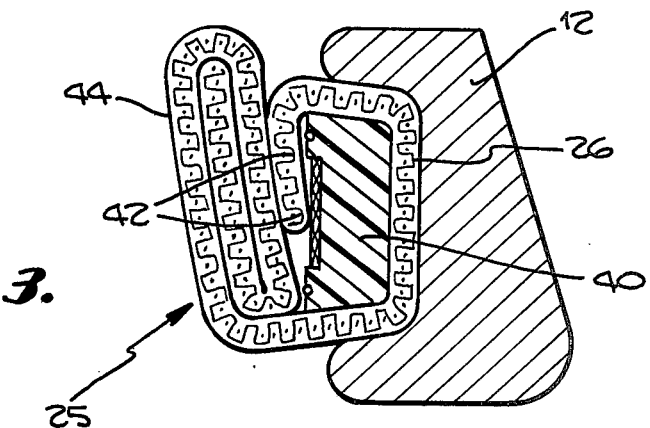
FIG. 3 is an enlarged cross-sectional view of a portion of the base and suturing cuff of the heart valve shown in FIG. 1, taken along the minor diameter of the cuff.

Referring particularly to FIG. 3 and FIG. 4, the suturing cuff 25 comprises a Teflon ring 40 upon which a plurality of monofilaments 42 have been wrapped so as to form an attachment point for threads and sutures which are used in the manufacturing of the cuff. The knitted seamless tubing 44 is folded so that its raw edges are inside the cuff. Each fold is sewed to the monofilaments 42. In general the procedure by which cuff 25 is manufactured includes placing a predetermined length of knitted seamless tubing 44 over the valve base 12. Teflon ring 40 is then applied over the knitted seamless tubing 44 and is received in retainer groove 26. Monofilaments 42, or other suitable thread size material, is then wrapped on the outer periphery of Teflon ring 40. The knitted seamless tubing 44 is then folded with each fold being attached to the monofilaments 42 by sewing (not illustrated). Additional layers of tubing material are provided along the major axis 34 to radially enlarge the cuff as illustrated, for example, in FIG. 4. These additional layers are integral with the rest of the material from which the cuff is formed. Various other operations may be performed such as, for example, various heat setting, sterilizing, inspection, and cleaning operations are required. The resultant cuff is rotatable relative to base 12 for optimum positioning of the valve after it has been sutured into place.

Referring paticularly to FIG. 5 and FIG. 6, knitted seamless tubing 44 is shown in its pre-folded configuration. The tubing is shown flattened with first and second removed panels 46 and 48, respectively, cut from tubing 44. The first and second integral ellipse forming panels 50 and 52, respectively, are adapted to be folded into the cuff to provide the extra material to radially enlarge the cuff 25 along major diameter 34. To form the cuff, a valve 10 is slipped into the cylindrical section 54 of tubing 44 and Teflon ring 40 is slipped over tubing 44 to midline 56 and into the cuff retainer groove 26, thus trapping tubing 44 between base 12 and ring 40. The elliptical cuff 25 is then formed by folding tubing 44 into the configuration shown in, for example, FIG. 1.

What have been described are preferred embodiments in which modifications and changes may be made without departing from the spirit and scope of the accompanying claims.

What is claimed is:

1. An elliptical prosthetic heart valve suturing cuff comprising:
   a knitted tubing consisting of biocompatible multifilament yarn materials, said knitted tubing being formed into a plurality of folds to form an elliptical suturing cuff and mounted on the exterior of a round planform prosthetic heart valve, said knitted tubing including excess materials at predetermined spaced apart locations whereby said suturing cuff is radially enlarged at predetermined spaced apart locations to define an elliptical planform suturing cuff, said knitted tubing being one integral piece of material with wales extending substantially longitudinally of said tubing, said wales being positioned in substantially vertical alignment from one fold to the next and said suturing cuff having a substantially uniform porosity throughout.

2. An elliptical prosthetic heart valve suturing cuff according to claim 1 wherein said valve includes passage therein, and there is a round planform freefloating disc restrained within said passage so as to be free to move responsive to the flow of fluid through said passage between open and closed positions by pivoting generally chordally within said passage and to rotate about its own axis of rotation.

3. An elliptical prosthetic heart valve suturing cuff of claim 1 wherein said elliptical planform suturing cuff has a minor diameter and a major diameter and the ratio of the length of said minor diameter to the length of said major diameter is from about 0.80 to 0.93.

4. An elliptical prosthetic heart valve suturing cuff of claim 2 wherein said elliptical planform suturing cuff has a minor diameter and a major diameter and said major diameter extends approximately parallel to an instantaneous chord about which said disc pivots.

5. An elliptical prosthetic heart valve suturing cuff of claim 1 wherein said prosthetic heart valve is a mitral valve.

* * * * *